US010238306B2

(12) United States Patent
Parfyonov et al.

(10) Patent No.: US 10,238,306 B2
(45) Date of Patent: Mar. 26, 2019

(54) METHOD FOR NON-EVASIVELY DETERMINING AN ENDOTHELIAL FUNCTION AND A DEVICE FOR CARRYING OUT SAID METHOD

(75) Inventors: Alexander Sergeevich Parfyonov, Moscow (RU); Maria Alexandrovna Parfyonova, Moscow (RU)

(73) Assignee: Everist Genomics, Inc., Anne Arbor, MI (US)

(*) Notice: Subject to any disclaimer, the term of this patent is extended or adjusted under 35 U.S.C. 154(b) by 1350 days.

(21) Appl. No.: 12/279,939

(22) PCT Filed: Apr. 3, 2006

(86) PCT No.: PCT/RU2006/000158
§ 371 (c)(1),
(2), (4) Date: Aug. 10, 2010

(87) PCT Pub. No.: WO2007/097654
PCT Pub. Date: Aug. 30, 2007

(65) Prior Publication Data
US 2010/0298717 A1    Nov. 25, 2010

(30) Foreign Application Priority Data

Feb. 20, 2006   (RU) .............................. 2006105107

(51) Int. Cl.
*A61B 5/02*      (2006.01)
*A61B 5/029*     (2006.01)
(Continued)

(52) U.S. Cl.
CPC .......... *A61B 5/029* (2013.01); *A61B 5/02007* (2013.01); *A61B 5/0295* (2013.01);
(Continued)

(58) Field of Classification Search
CPC ..... A61B 5/021; A61B 5/022; A61B 5/02233; A61B 5/0295; A61B 5/02116;
(Continued)

(56) References Cited

U.S. PATENT DOCUMENTS 3,807,389 A   4/1974   Miller et al.
3,903,872 A   9/1975   Link
(Continued)

FOREIGN PATENT DOCUMENTS

DE   102004016376 A1   10/2005
EP       0197302 A2    10/1986
(Continued)

OTHER PUBLICATIONS

International Search Report and Written Opinion dated Jul. 6, 2010 regarding PCT/US2010/033907 with a filing date on May 6, 2010.
(Continued)

*Primary Examiner* — Puya Agahi
(74) *Attorney, Agent, or Firm* — Dykema Gossett PLLC

(57) ABSTRACT

The invention relates to medicine. The inventive method for non-evasively determining an endothelial function consists in reducing a transmural pressure in a limb, recording the amplitude of plethysmographic signals at different pressures, determining the pressure of a maximum plethysmographic signal amplitude, reducing the pressure to a value corresponding to the specified percentage of the maximum amplitude, carrying out an occlusion sample in the course of which a pressure higher by at least 50 mm Hg than the systolic pressure of a tested patient is produced in a cuff arranged proximally to the located limb area, wherein the occlusion is carried out during at least 5 minutes. The inventive device for carrying out said method comprises a sensory unit, a pressure producing unit, an electronic unit constructed in such a way that it makes it possible to
(Continued)

measure the cuff pressure corresponding to the maximum plethysmographic signal amplitude and a unit for controlling the pressure producing unit in such a way that the cuff pressure corresponding to the amplitude of a plethysmographic signal, which represents a specified percentage of the maximum amplitude, is attained. The sensory unit is connected to the electronic unit to the output of which the pressure producing unit is connected.

11 Claims, 4 Drawing Sheets

(51) Int. Cl.
*A61B 5/0295* (2006.01)
*A61B 5/021* (2006.01)
*A61B 5/024* (2006.01)
*A61B 5/022* (2006.01)
*A61B 5/00* (2006.01)

(52) U.S. Cl.
CPC ...... *A61B 5/02116* (2013.01); *A61B 5/02422* (2013.01); *A61B 5/021* (2013.01); *A61B 5/022* (2013.01); *A61B 5/02233* (2013.01); *A61B 5/02416* (2013.01); *A61B 5/7275* (2013.01)

(58) Field of Classification Search
CPC ............ A61B 5/02416; A61B 5/02255; A61B 5/02007; A61B 5/02422
USPC ........ 600/301, 483, 490–492, 494–500, 504, 600/323, 324, 465, 479–481, 485
See application file for complete search history.

(56) References Cited

U.S. PATENT DOCUMENTS

| | | | |
|---|---|---|---|
| 3,980,075 A | 9/1976 | Heule | |
| 4,009,709 A | 3/1977 | Link et al. | |
| 4,074,711 A | 2/1978 | Link et al. | |
| 4,163,447 A | 8/1979 | Orr | |
| 4,195,643 A | 4/1980 | Pratt, Jr. | |
| 4,406,289 A * | 9/1983 | Wesseling et al. | 600/483 |
| 4,432,374 A | 2/1984 | Osanai | |
| 4,510,940 A * | 4/1985 | Wesseling | 600/480 |
| 4,539,997 A * | 9/1985 | Wesseling et al. | 600/480 |
| 4,562,843 A | 1/1986 | Djordjevich et al. | |
| 4,566,463 A | 1/1986 | Taniguchi et al. | |
| 4,646,754 A | 3/1987 | Seale | |
| 4,669,485 A | 6/1987 | Russell | |
| 4,677,983 A | 7/1987 | Yamaguchi et al. | |
| 4,718,426 A | 1/1988 | Russell | |
| 4,718,427 A | 1/1988 | Russell | |
| 4,718,428 A | 1/1988 | Russell | |
| 4,771,792 A | 9/1988 | Seale | |
| 4,798,211 A | 1/1989 | Goor et al. | |
| 4,821,735 A | 4/1989 | Goor et al. | |
| 4,846,189 A | 7/1989 | Sun | |
| 4,850,371 A | 7/1989 | Broadhurst et al. | |
| 4,880,013 A | 11/1989 | Chio | |
| 4,966,141 A | 10/1990 | Bacaner et al. | |
| 4,979,110 A | 12/1990 | Albrecht et al. | |
| 4,986,277 A | 1/1991 | Sackner | |
| 4,993,422 A | 2/1991 | Hon et al. | |
| 5,025,792 A | 6/1991 | Hon et al. | |
| 5,040,540 A | 8/1991 | Sackner | |
| 5,043,576 A | 8/1991 | Broadhurst et al. | |
| 5,048,533 A | 9/1991 | Muz | |
| 5,054,494 A | 10/1991 | Lazzaro et al. | |
| 5,099,852 A | 3/1992 | Meister et al. | |
| 5,119,824 A | 6/1992 | Niwa | |
| 5,127,408 A | 7/1992 | Parsons et al. | |
| 5,140,990 A | 8/1992 | Jones et al. | |
| 5,152,297 A | 10/1992 | Meister et al. | |
| 5,161,531 A | 11/1992 | Parsons et al. | |
| 5,162,991 A | 11/1992 | Chio | |
| 5,241,963 A | 9/1993 | Shankar | |
| 5,241,964 A | 9/1993 | McQuilkin | |
| 5,269,310 A | 12/1993 | Jones et al. | |
| 5,271,399 A | 12/1993 | Listerud et al. | |
| 5,297,556 A | 3/1994 | Shankar | |
| 5,303,711 A | 4/1994 | Sciarra | |
| 5,343,867 A | 9/1994 | Shankar | |
| 5,379,774 A | 1/1995 | Nishimura et al. | |
| 5,423,322 A | 6/1995 | Clark et al. | |
| 5,447,163 A | 9/1995 | Apple | |
| 5,485,838 A * | 1/1996 | Ukawa et al. | 600/330 |
| 5,511,546 A | 4/1996 | Hon | |
| 5,533,511 A | 7/1996 | Kaspari et al. | |
| 5,685,989 A | 11/1997 | Krivitski et al. | |
| 5,758,652 A | 6/1998 | Nikolic | |
| 5,810,734 A | 9/1998 | Caro et al. | |
| 5,830,131 A | 11/1998 | Caro et al. | |
| 5,833,602 A | 11/1998 | Osemwota | |
| 5,876,347 A | 3/1999 | Chesney et al. | |
| 5,906,581 A | 5/1999 | Tsuda | |
| 5,935,066 A | 8/1999 | Harris | |
| 5,961,467 A * | 10/1999 | Shimazu et al. | 600/485 |
| 5,980,464 A | 11/1999 | Tsuda | |
| 6,010,457 A | 1/2000 | O'Rourke | |
| 6,015,393 A | 1/2000 | Hovland et al. | |
| 6,027,452 A | 2/2000 | Flaherty et al. | |
| 6,045,509 A | 4/2000 | Caro et al. | |
| 6,048,318 A | 4/2000 | Chesney et al. | |
| 6,088,607 A * | 7/2000 | Diab et al. | 600/322 |
| 6,120,459 A * | 9/2000 | Nitzan | A61B 5/02125 600/485 |
| 6,152,881 A | 11/2000 | Raines et al. | |
| 6,162,181 A | 12/2000 | Hynson et al. | |
| 6,171,242 B1 | 1/2001 | Amano et al. | |
| 6,210,591 B1 | 4/2001 | Krivitski | |
| 6,241,680 B1 | 6/2001 | Miwa | |
| 6,290,651 B1 | 9/2001 | Chesney et al. | |
| 6,309,359 B1 | 10/2001 | Whitt et al. | |
| 6,319,205 B1 | 11/2001 | Goor et al. | |
| 6,322,515 B1 | 11/2001 | Goor | |
| 6,331,159 B1 | 12/2001 | Amano et al. | |
| 6,331,161 B1 | 12/2001 | Chesney et al. | |
| 6,338,719 B1 | 1/2002 | Drzewiecki et al. | |
| 6,440,080 B1 | 8/2002 | Booth et al. | |
| 6,445,945 B1 | 9/2002 | Arsenault | |
| 6,461,305 B1 | 10/2002 | Schnall | |
| 6,482,163 B2 | 11/2002 | Oka et al. | |
| 6,488,633 B1 | 12/2002 | Schnall | |
| 6,488,663 B1 | 12/2002 | Steg | |
| 6,491,647 B1 | 12/2002 | Bridger et al. | |
| 6,517,495 B1 | 2/2003 | Hersh | |
| 6,554,774 B1 | 4/2003 | Miele | |
| 6,585,659 B1 | 7/2003 | Chesney et al. | |
| 6,592,528 B2 | 7/2003 | Amano | |
| 6,616,613 B1 | 9/2003 | Goodman | |
| 6,623,431 B1 | 9/2003 | Sakuma et al. | |
| 6,623,434 B2 | 9/2003 | Chesney et al. | |
| 6,626,840 B2 | 9/2003 | Drzewiecki et al. | |
| 6,662,130 B1 | 9/2003 | Peel, III et al. | |
| 6,629,343 B1 | 10/2003 | Chesney et al. | |
| 6,632,181 B2 | 10/2003 | Flaherty et al. | |
| 6,654,628 B1 | 11/2003 | Silber et al. | |
| 6,719,704 B2 | 4/2004 | Narimatsu et al. | |
| 6,733,461 B2 | 5/2004 | Bratteli | |
| 6,746,407 B2 | 6/2004 | Steuer et al. | |
| 6,749,567 B2 | 6/2004 | Davis et al. | |
| 6,757,554 B2 | 6/2004 | Rubinstein et al. | |
| 6,804,543 B2 | 10/2004 | Miller et al. | |
| 6,868,739 B1 | 3/2005 | Krivitski et al. | |
| 6,884,221 B2 | 4/2005 | Narimatsu et al. | |
| 6,896,660 B2 | 5/2005 | Jelliffe et al. | |
| 6,905,470 B2 | 6/2005 | Lee et al. | |
| 6,908,436 B2 * | 6/2005 | Chowienczyk | A61B 5/02125 600/485 |
| 6,915,154 B1 | 7/2005 | Docherty et al. | |
| 6,916,289 B2 | 7/2005 | Schnall | |
| 6,937,882 B2 | 8/2005 | Steuer et al. | |

(56) References Cited

U.S. PATENT DOCUMENTS

| | | |
|---|---|---|
| 6,939,304 B2 | 9/2005 | Schnall et al. |
| 6,939,305 B2 | 9/2005 | Flaherty et al. |
| 6,976,966 B2 * | 12/2005 | Narimatsu .................. 600/494 |
| 6,987,993 B2 | 1/2006 | Steuer et al. |
| 6,994,675 B2 | 2/2006 | Sharrock |
| 7,022,084 B2 | 4/2006 | Ogura |
| 7,024,234 B2 | 4/2006 | Margulies et al. |
| 7,041,060 B2 | 5/2006 | Flaherty et al. |
| 7,048,691 B2 | 5/2006 | Miele et al. |
| 7,056,291 B2 | 6/2006 | Yokozeki et al. |
| 7,070,569 B2 | 7/2006 | Heinonen et al. |
| 7,074,183 B2 | 7/2006 | Castellanos |
| 7,077,809 B2 | 7/2006 | Wu et al. |
| 7,121,150 B2 | 10/2006 | Krivitski et al. |
| 7,131,949 B2 | 11/2006 | Hayano et al. |
| 7,204,798 B2 | 4/2007 | Zdeblick et al. |
| 7,214,192 B2 | 5/2007 | Poliac et al. |
| 7,244,225 B2 | 7/2007 | Loeb et al. |
| 7,250,031 B2 | 7/2007 | Hayano et al. |
| 7,264,594 B2 | 9/2007 | Shimazu et al. |
| 7,291,112 B2 | 11/2007 | Martin et al. |
| 7,291,113 B2 | 11/2007 | Satoh et al. |
| 7,297,280 B2 | 11/2007 | Krivitski et al. |
| 7,318,804 B2 | 1/2008 | Weitzel et al. |
| 7,374,541 B2 | 5/2008 | Amitzur et al. |
| 7,621,877 B2 | 11/2009 | Schnall |
| 7,806,831 B2 | 10/2010 | Lavie et al. |
| 2001/0025151 A1 | 9/2001 | Kimball et al. |
| 2002/0013533 A1 | 1/2002 | Oka et al. |
| 2002/0062086 A1 | 5/2002 | Miele et al. |
| 2002/0065471 A1 | 5/2002 | Amano et al. |
| 2002/0072681 A1 | 6/2002 | Schnall |
| 2002/0111554 A1 | 8/2002 | Drzewiecki et al. |
| 2002/0183599 A1 | 12/2002 | Castellanos |
| 2003/0004423 A1 | 1/2003 | Lavie et al. |
| 2003/0032885 A1 | 2/2003 | Rubinstein et al. |
| 2003/0036685 A1 | 2/2003 | Goodman |
| 2003/0040675 A1 | 2/2003 | Sharrock |
| 2003/0060690 A1 | 3/2003 | Jelliffe et al. |
| 2003/0065270 A1 | 4/2003 | Raines et al. |
| 2003/0069507 A1 * | 4/2003 | Nishibayashi .............. 600/485 |
| 2003/0191395 A1 | 10/2003 | Bowman et al. |
| 2003/0212336 A1 | 11/2003 | Lee et al. |
| 2003/0216652 A1 | 11/2003 | Narimatsu et al. |
| 2003/0229288 A1 | 12/2003 | Chowienczyk et al. |
| 2003/0236464 A1 | 12/2003 | Narimatsu et al. |
| 2004/0064057 A1 * | 4/2004 | Siegel ......................... 600/500 |
| 2004/0092832 A1 | 5/2004 | Schnall et al. |
| 2004/0116787 A1 | 6/2004 | Schnall |
| 2004/0127800 A1 | 7/2004 | Kimball et al. |
| 2004/0167413 A1 | 8/2004 | Bratteli |
| 2004/0215085 A1 | 10/2004 | Schnall |
| 2004/0215093 A1 | 10/2004 | Rubinstein et al. |
| 2004/0230125 A1 | 11/2004 | Amano et al. |
| 2004/0254483 A1 | 12/2004 | Zdeblick et al. |
| 2004/0254485 A1 * | 12/2004 | Wu et al. .................... 600/490 |
| 2004/0267141 A1 | 12/2004 | Amano et al. |
| 2005/0004476 A1 | 1/2005 | Payvar et al. |
| 2005/0010928 A1 | 1/2005 | Arsenault |
| 2005/0020891 A1 | 1/2005 | Rubinstein et al. |
| 2005/0038346 A1 | 2/2005 | Miele |
| 2005/0043608 A1 | 2/2005 | Haj-Yousef |
| 2005/0070805 A1 * | 3/2005 | Dafni .................. A61B 5/02007 |
| | | 600/492 |
| 2005/0075531 A1 | 4/2005 | Loeb et al. |
| 2005/0085712 A1 | 4/2005 | Rapoport |
| 2005/0107710 A1 | 5/2005 | Nakayama |
| 2005/0113652 A1 | 5/2005 | Stark et al. |
| 2005/0143633 A1 | 6/2005 | Jelliffe et al. |
| 2005/0171443 A1 | 8/2005 | Gorenberg et al. |
| 2005/0182434 A1 | 8/2005 | Docherty et al. |
| 2005/0228303 A1 | 10/2005 | Hayano et al. |
| 2005/0256412 A1 * | 11/2005 | Shimazu ................ A61B 5/022 |
| | | 600/500 |
| 2005/0267381 A1 | 12/2005 | Benditt et al. |
| 2006/0009688 A1 * | 1/2006 | Lamego ............ A61B 5/14551 |
| | | 600/323 |
| 2006/0009700 A1 | 1/2006 | Brumfield et al. |
| 2006/0015032 A1 | 1/2006 | Gordon |
| 2006/0052713 A1 | 3/2006 | Poliac et al. |
| 2006/0052714 A1 * | 3/2006 | Poliac et al. .................. 600/492 |
| 2006/0064024 A1 | 3/2006 | Schnall |
| 2006/0079791 A1 | 4/2006 | Letremy et al. |
| 2006/0104824 A1 | 5/2006 | Schnall |
| 2006/0122489 A1 | 6/2006 | Kato et al. |
| 2006/0149152 A1 | 7/2006 | Amitzur et al. |
| 2006/0178585 A1 | 8/2006 | Sharrock |
| 2006/0206030 A1 | 9/2006 | Flaherty et al. |
| 2006/0206032 A1 | 9/2006 | Miele et al. |
| 2006/0217614 A1 | 9/2006 | Takala et al. |
| 2006/0217615 A1 | 9/2006 | Huiku et al. |
| 2006/0229488 A1 | 10/2006 | Ayre et al. |
| 2006/0229506 A1 | 10/2006 | Castellanos |
| 2006/0229519 A1 | 10/2006 | Fujiwara et al. |
| 2006/0241459 A1 | 10/2006 | Tai |
| 2006/0247538 A1 | 11/2006 | Davis |
| 2006/0258946 A1 | 11/2006 | Hayano et al. |
| 2006/0264755 A1 | 11/2006 | Maltz et al. |
| 2006/0287600 A1 | 12/2006 | McEowen |
| 2007/0021673 A1 | 1/2007 | Arbel et al. |
| 2007/0021683 A1 | 1/2007 | Benditt et al. |
| 2007/0055163 A1 | 3/2007 | Asada et al. |
| 2007/0078351 A1 | 4/2007 | Fujita et al. |
| 2007/0106162 A1 | 5/2007 | Illyes et al. |
| 2007/0118045 A1 | 5/2007 | Naghavi et al. |
| 2007/0161914 A1 | 7/2007 | Zdeblick et al. |
| 2007/0173727 A1 | 7/2007 | Naghavi et al. |
| 2007/0225606 A1 | 9/2007 | Naghavi et al. |
| 2007/0270720 A1 | 11/2007 | Fry |
| 2008/0004511 A1 | 1/2008 | Rubenstein et al. |
| 2008/0013777 A1 * | 1/2008 | Park ..................... A61B 5/0059 |
| | | 381/384 |
| 2008/0015434 A1 | 1/2008 | Rubenstein et al. |
| 2008/0027298 A1 | 1/2008 | Blanco et al. |
| 2008/0027330 A1 | 1/2008 | Naghavi et al. |
| 2008/0033307 A1 | 2/2008 | Baudoin et al. |
| 2008/0039731 A1 | 2/2008 | McCombie et al. |
| 2008/0077024 A1 | 3/2008 | Schnall |
| 2008/0139949 A1 | 6/2008 | Caldarone et al. |

FOREIGN PATENT DOCUMENTS

| | | |
|---|---|---|
| EP | 0244264 A1 | 11/1987 |
| EP | 0262778 A1 | 4/1988 |
| EP | 0347101 A2 | 12/1989 |
| EP | 0443267 A1 | 8/1991 |
| EP | 0694283 A2 | 1/1996 |
| EP | 0716829 A2 | 6/1996 |
| EP | 0818175 A1 | 1/1998 |
| EP | 0997102 A1 | 5/2000 |
| EP | 1175864 A2 | 1/2002 |
| EP | 1360929 A1 | 11/2003 |
| EP | 1362549 A2 | 11/2003 |
| EP | 1374760 A2 | 1/2004 |
| EP | 1584289 A2 | 10/2005 |
| EP | 1618840 A1 | 1/2006 |
| EP | 1704818 A2 | 9/2006 |
| EP | 1743572 A1 | 1/2007 |
| EP | 1769748 A1 | 4/2007 |
| EP | 1849408 A2 | 10/2007 |
| EP | 1852061 A1 | 11/2007 |
| EP | 1852063 A1 | 11/2007 |
| IL | 120109 | 12/2002 |
| IL | 120881 | 12/2002 |
| IL | 151437 | 9/2007 |
| IL | 154833 | 9/2007 |
| JP | 5305061 A | 11/1993 |
| JP | 2938237 B2 | 6/1996 |
| JP | 9173307 A | 7/1997 |
| JP | 2004129979 A | 4/2004 |
| JP | 2006102252 A | 4/2006 |
| JP | 2006115979 A | 5/2006 |
| JP | 2006181261 A | 7/2006 |
| RU | 2220653 C2 | 1/2004 |

(56) References Cited

FOREIGN PATENT DOCUMENTS

| | | |
|---|---|---|
| RU | 2265391 C2 | 7/2005 |
| RU | 2004102316 A | 7/2005 |
| RU | 2302196 C2 | 7/2007 |
| WO | 8604801 A1 | 8/1986 |
| WO | 8909017 A1 | 10/1989 |
| WO | 9001895 A1 | 3/1990 |
| WO | 9002512 A1 | 3/1992 |
| WO | 9207508 A1 | 5/1992 |
| WO | 9222239 A1 | 12/1992 |
| WO | 9305704 A1 | 4/1993 |
| WO | 9518564 A1 | 7/1995 |
| WO | 9709927 A2 | 3/1997 |
| WO | 9712545 A2 | 4/1997 |
| WO | 9714356 A1 | 4/1997 |
| WO | 9749328 A1 | 12/1997 |
| WO | 9804182 A2 | 2/1998 |
| WO | 9842255 A1 | 10/1998 |
| WO | 9934724 A2 | 7/1999 |
| WO | 9939634 A1 | 8/1999 |
| WO | 9963884 A1 | 12/1999 |
| WO | 0017615 A2 | 3/2000 |
| WO | 0032103 A1 | 6/2000 |
| WO | 0057776 A1 | 10/2000 |
| WO | 0059372 A1 | 10/2000 |
| WO | 0074551 A2 | 12/2000 |
| WO | 0074563 A1 | 12/2000 |
| WO | 0122870 A1 | 4/2001 |
| WO | 0164101 A1 | 9/2001 |
| WO | 0170303 A2 | 9/2001 |
| WO | 0195798 A2 | 12/2001 |
| WO | 2002000107 A2 | 1/2002 |
| WO | 2002005726 A2 | 1/2002 |
| WO | 2002034105 A2 | 5/2002 |
| WO | WO 02/34105 A2 | 5/2002 |
| WO | 02/085204 A2 | 10/2002 |
| WO | 2002080752 A2 | 10/2002 |
| WO | 2002089668 A1 | 11/2002 |
| WO | 2002094085 A2 | 11/2002 |
| WO | 2002099600 A2 | 12/2002 |
| WO | 2003051193 A1 | 6/2003 |
| WO | 2003086169 A2 | 10/2003 |
| WO | WO 2003/086169 A2 | 10/2003 |
| WO | 2004006748 A3 | 1/2004 |
| WO | 2004021878 A1 | 3/2004 |
| WO | 2004041079 A1 | 5/2004 |
| WO | 2004052196 A1 | 6/2004 |
| WO | 2004066817 A3 | 8/2004 |
| WO | 2005006975 A1 | 1/2005 |
| WO | 2005028029 A3 | 3/2005 |
| WO | 2005030038 A3 | 4/2005 |
| WO | 2005092178 A1 | 10/2005 |
| WO | 2005110051 A2 | 11/2005 |
| WO | 2006024871 A1 | 3/2006 |
| WO | 2006034542 A1 | 6/2006 |
| WO | 2006102511 A2 | 9/2006 |
| WO | 2007024777 A2 | 3/2007 |
| WO | 2009144598 A1 | 12/2009 |
| WO | 2009144721 A2 | 12/2009 |
| WO | 2010089745 A2 | 8/2010 |

OTHER PUBLICATIONS

Tsui, et al., Arterial pulse waveform analysis by the probability distribution of amplitude, 2007, vol. 28, No. 8, Physiological Measurement—attached as reference to International Search Report and Written Opinion dated Jul. 6, 2010 regarding PCT/US2010/033907.

Semkin, ND, Diagnosis of vascular endothelial function in patients with cardiovascular disease Methodological guidelines, 2004, 17 pp., Samara State Aerospace University.

Supplementary Search Report of EP Application No. 06784054.6, dated Aug. 8, 2009, 6 pages total.

International Preliminary Report on Patentability of PCT Application No. PCT/RU2006/000158, dated Dec. 10, 2008, 8 pages total.

\* cited by examiner

METHOD FOR NON-EVASIVELY DETERMINING AN ENDOTHELIAL FUNCTION AND A DEVICE FOR CARRYING OUT SAID METHOD

BACKGROUND OF THE INVENTION

Area of Application

The invention applies to medicine, particularly to functional diagnostics, and allows early detection of cardiovascular diseases as well as the monitoring of the effectiveness of treatment received by the patient. The invention assesses the state of endothelial function and, based on this assessment, addresses the need of early diagnosis of cardiovascular disease. This invention can be used for widespread testing of the population.

Prior Art

As of late, the need for early cardiovascular disease detection has become more and more relevant. For this end a wide spectrum of means and methods described in patent and scientific literature is used. For example, the U.S. Pat. No. 5,343,867 describes a method and apparatus for early diagnosis of atherosclerosis using impedance plethysmography to detect an irregular pulse wave in the arteries of the lower extremities. It is shown that blood flow parameters depend on the outside pressure applied to the artery under investigation. The maximum amplitude of the plethysmogram is in large determined by the size of the transmural pressure, which is defined as the difference between internal arterial pressure and the pressure applied externally by the cuff. Maximum amplitude is reached when the transmural pressure drops to zero.

From the perspective of the structure and physiology of blood vessels, this can be imagined to occur in the following manner: Pressure from the cuff transfers to the exterior of the artery and counterbalances the pressure of the interior of the artery wall. With this, the compliance of the arterial wall increases dramatically and the passing pulse wave stretches the artery to a large diameter, i.e. the increase of the arterial diameter at the same pulse pressure becomes significant. This phenomenon can be observed on an oscillometric curve, recorded during the taking of arterial pressure. The peak of the oscillometric curve corresponds to the moment when the pressure inside the cuff equals the mean arterial pressure.

U.S. Pat. No. 6,322,515 describes a method and apparatus for determining a set of cardiovascular parameters which are used for the evaluation of the state of endothelial function. Photodiodes and photoreceptors are used as pulse wave sensors, and an analysis of photo-plethysmographic waveforms is made. The measurements for these waveforms are taken at the observed artery before and after the test with reactive hyperemia. During the recording of these waveforms, the cuff, where the pressure is maintained at 70 mmHg, is placed on the digit, over the optical sensor.

U.S. Pat. No. 6,939,304 reveals a method and apparatus for non-invasive assessment of endothelial function using the photoplethysmography (PPG) sensor.

U.S. Pat. No. 6,908,436 reveals a method for the assessment of endothelial function by measuring the spreading of the pulse wave. For this a two-channel plethysmograph is used, sensors are mounted on one of the phalanges of the finger, and an occlusion is created with the help of the cuff placed on the shoulder. Changes in the state of the arterial wall are assessed based on the duration of delay in the spreading of the pulse wave. If the duration of the delay is 20 ms or longer, the delay is considered to confirm normal endothelial function. The duration of the delay is established by comparing it with the PPG waveform which is measured on the arm not influenced by the occlusion test. However, this method falls short when it comes to determining the delay of displacement in the area of the minimum directly before systolic growth, i.e. in the area which is to a significant extent variable.

The most analogous method and apparatus to the one described below is the method and apparatus for non-invasive evaluation of the physical state of the patient described in patent #2,220,653 of the Russian Federation. The method consists of the following: First a control of the peripheral arterial tone is established by distributing the pulse of the cuff across several sensors and raising the pressure in the cuff to 75 mmHg. Then arterial pressure is measured by raising the pressure in the cuff above the systolic pressure and keeping it there for five minutes. Pulse wave measurements are further taken on both arms by the PPG method. Finally the PPG waveform is analyzed with regard to its amplitude by comparing its values before and after the occlusion and determining the increase of the measured output. This apparatus includes a sensor for measuring pressure with the cuff, a heating element for heating the surface of the observed region of the body, and a processor for processing the measured output.

However, this method and this apparatus are not able to provide reliable results due to the low precision of measurements and their dependency on the fluctuating blood pressure of the patient.

BRIEF SUMMARY OF THE INVENTION

The endothelial dysfunction occurs in the presence of various risk factors for cardiovascular disease (CVD), such as high cholesterol levels, arterial hypertension, smoking, age and others. It is established that endothelial cells is the organ-target for the pathogenic realization of factors contributing to the risk of CVD development. The assessment of endothelial function acts as the "barometer" which allows early diagnosis of CVD. Such a diagnostic approach will allow a departure from the current approach were a set of biochemical tests must be administered to the patient (determining the levels of cholesterol, high and low-density lipoproteins, and others) in order to detect the presence of risk factors. During the early stages of CVD it is economically sound to screen the population using internal indicators for the risk of disease development. One such indicator is the state of endothelial function. The assessment of this state is also extremely relevant for the quality assessment of received therapies.

The goal of this invention is to create a physiologically-based non-invasive method and apparatus for reliably determining the state of endothelial function in the patient. This method and apparatus will offer an individualized approach based on the particular conditions of the patient. The method and apparatus will be based on a system of conversion, amplification, and recording of the PPG output during the onset of the optimal magnitude of the established pressure or pressure locally applied to the observed artery before and after the occlusion test.

The technical result, which is achieved with the use of the aforementioned device and apparatus, is centered on reliable assessment of endothelial function regardless of the arterial pressure of the patient.

In terms of method, the technical result is achieved through a series of steps. First, the transmural pressure in the artery is lowered. Then the amplitude of plethysmographic output is measured at various pressures. Once the pressure at which the amplitude of the PG signal is maximal is established, the pressure is lowered to a predetermined percentage of the maximal amplitude. Finally, an occlusion test is performed for at least five minutes. During this test a pressure is created in the cuff which is placed on the observed region of the extremity. This pressure must exceed the measured systolic pressure by at least 50 mmHg.

The technical result is amplified because the transmural pressure is lowered when the pressure-generating cuff is placed on a particular region of the extremity.

The pressure on the extremity is raised gradually every five to ten seconds by increments of 5 mmHg. At each step the amplitude of the PG output is measured and recorded.

A mechanical pressure is locally applied to the extremity in order to lower the transmural pressure in the observed artery.

In order to lower the transmural pressure in the observed artery, the hydrostatic pressure is lessened by raising the extremity a specified height above the level of the heart.

The intensity of the transmural pressure is established when the amplitude of the PG output is 50% that of the maximal PG output. This pressure is created in the cuff which is placed in close proximity to the observed artery. Then super-systolic pressure is created and the plethysmographic output is recorded.

After at least five minutes of exposure to the occlusion cuff placed near the observed artery, the pressure in the cuff is lowered to zero. The changes in the PG output reading are recorded simultaneously by the reference channel and the monitoring channel for at least five minutes.

After the occlusion test, the recorded plethysmographic signal is analyzed using both the amplitudal and timely analyses based on the data collected through the reference and monitoring channels.

During the amplitudal analysis the heights of the amplitude of the output from the reference channel are compared to those collected from the monitoring channel. Also, the growth rate of the amplitude in the monitoring channel is analyzed. Finally, the amplitude of the output recorded during various transmural pressures is compared to the maximal amplitude of the output recorded after the running of the occlusion test.

During the timely analysis, plethysmogrphic waveforms collected through the reference and monitoring channels are compared. The output is then normalized and the delay time or phase change is determined.

The technical result in the device is achieved by the three parts, or blocks, of the device. The first of these is a double-channeled sensor block which detects pulse wave signals from peripheral arteries. The second is a pressure block which creates gradually increasing pressure in the blood pressure cuff. The final block is an electronic block which measures the pressure created in the cuff. This pressure corresponds to the maximal amplitude of the PG signal. Along with measuring pressure in the blood pressure cuff, the electronic block also operates the pressure block, which creates pressure in the cuff equal to an assigned percentage of the increase in maximal amplitude. The sensor block is connected to the electronic block, which is in turn hooked up through an outlet to the pressure block.

The technical result is amplified because the pressure block is able to create pressure which is increased gradually by increments of 5 mmHg and time increments of five to ten seconds, in the cuff.

The sensor block in each channel includes an infrared diode and a photoreceptor. Both of these devices are situated so that they are able to read the light signal passing through the observed field.

The infrared diode and the light receptor are also able to sense and record the diffused light signal reflected off the observed field.

The sensor block also includes impedancemetric electrodes, or Hall sensors, or an elastic tube filled with electroconductive material.

The light receptor is connected to a filter which filters pulse wave component out of the general signal.

The device also includes orthogonally-placed polarized filters which protect the photoreceptor from extraneous exposure to light.

The sensor block finally includes a means for maintaining a set temperature of the observed region of the body.

The device has either a liquid-crystal screen for displaying the results of endothelial tissue assessment, or an interface system connected to the electronic block for transferring the collected data to a computer.

BRIEF DESCRIPTION OF THE DRAWINGS

The essence of the invention and its ability to provide certain results will be easier understood through an example of usage. In this example there will be references made to the drawings below.

FIG. 3 shows a PPG curve while

Finally.

DETAILED DESCRIPTION OF THE INVENTION

Figure 6:
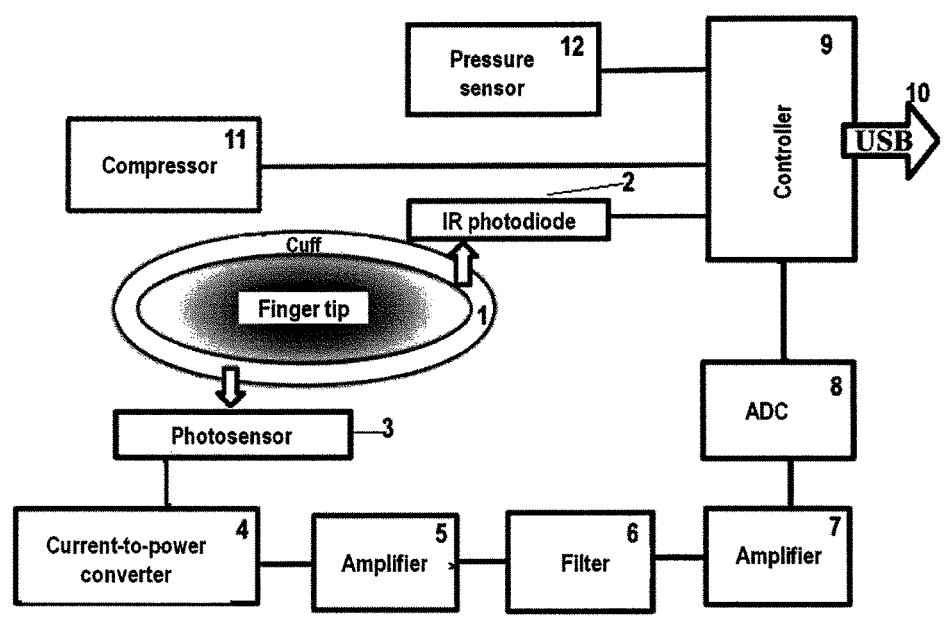
FIG. 6 shows the major block diagram of the device.

The apparatus (FIG. 6) is used for assessing the function of endothelial tissue. The device includes a double-channeled sensor block (for simplicity the double channel is shown as single in the figures). Each of the channels has an infrared light diode (2) which is connected to the output of the control (9). It also includes a photoreceptor connected to the input of the electric voltage converter (4). The sensor block records pulse waveforms from peripheral arteries. The pressure block includes a compressor (11), which creates pressure in the cuff (1). This compressor is controlled by the control (9). The pressure block also has a pressure sensor (12) for recording the patient's blood pressure. This pressure sensor (12) is attached to the output of the control (9). Apart from this, the pressure block can be used as a means for applying mechanical pressure on a particular section of an extremity. The electronic block has a programmable control (9), programmed for operating the compressor (11) and turning on the light diode (2), as well as for processing data coming in from the light receptor chain. The input to the control (9) is connected to the output of the pressure sensor (12), which in turn is connected to the converter (4) of the digital analog converter (8) through a sequence of amplifier (5), filter (6), and scalar amplifier (7). On top of that, the control (9) is connected through a set of input-output linkages to a USB interface for connecting to an external computer (not shown). The photoreceptor (3) signal is converted as it moves through a chain of mechanisms which include the converter (4), amplifiers (5 and 7), and filter (6) which can filter the pulse signal out from the overall noise. The device also includes orthogonally-stationed polarized filters (not shown) for filtering out extraneous light which could overexpose the photoreceptor (3). Finally, the device has, in its sensor block, a means of maintaining an assigned temperature of the observed region of the body, as well as a liquid crystal screen connected to the control (9) which displays the results of endothelial function assessment. The cuff (1) is placed over the sensors (2 and 3). In the case where mechanical effort is needed, a drive (for example, one that turns on the panel which acts on the sensors) that is connected to the means of creating a mechanical pressure is placed over the two sensors instead of the cuff.

The electronic block defines the pressure in the cuff (1) which corresponds to the maximal amplitude of the PG signal. This block also controls the pressure block which generates pressure in the cuff (1) equal to a predetermined percentage (50%) of the maximal growth of the pressure magnitude. The sensor block can be created with two different variations. The first variation has the infrared light diode (2) and the photoreceptor (3) stationed on opposite sides of the observed region of the extremity in order to be able to record light signals passing through the observed field. The second variation has the infrared diode (2) and the photoreceptor (3) stationed on the same side of the observed vessel.

Also, the sensor block can be made with impedancemetric electrodes, Hall sensors, or an elastic tube filled with electroconductive material.

The assessment of endothelial function is founded on the PG output readings obtained by the sensor block which is set up on the upper extremity of the observed patient. The signal coming from the cuff is electrically converted as the pressure increases linearly in the cuff (1) until maximal amplitude of the signal is reached. After this the magnitude of the pressure in the cuff or the locally-applied pressure is fixed and the occlusion test is run. During this procedure the sensor block is set up on the internal side of the cuff (1) or is placed at the end of the device which applies pressure in the area where the artery protrudes on the surface of the skin. A reverse connection based on the amplitude of the PG output is used for automatically establishing the aforementioned pressure. During this procedure the PG signal is sent from the digital analog converter (8) through control (9) to the compressor (11) located in the pressure block.

The occlusion test is done using the cuff which is in close proximity (shoulder, forearm, wrist) to the observed artery (shoulder, radial, or digital artery) At the same time the signal received from the other extremity, where the occlusion test is not done, is used as a reference.

The method for assessing the state of endothelial activity of the observed patient has two major stages. During the first stage, a set of plethysmographic waveforms is recorded as the cuff (1) generates various pressures (or various pressures are applied to the observed artery). The second stage comprises the occlusion itself. The first stage provides information on the elastic qualities of the arterial channel. This information is then used to decide between applying cuff pressure or external pressure during the occlusion test. The measurements of the amplitude of the PG signal taken during the effects of the applied pressure describe the tone quality of smooth muscle in the artery as well as its elastic components (elastin and collagen). Locally-applied pressure us accompanied by changes in transmural pressure, whose magnitude is determined by the difference between arterial pressure and the externally applied pressure. When transmural pressure is weakened, the muscle tone of smooth muscle tissue lowers as well. This lowering is accompanied by the widening of arterial channels. Conversely, when transmural pressure is raised, the arteries become narrower. In this lies the myogenic regulation of blood flow, aimed at maintaining optimal pressure in the microcirculatory system. This is the reason why during changes in the magistral vessel from 150 mmHg to 50 mmHg, the capillary pressure remains practically unchanged.

Figure 4:
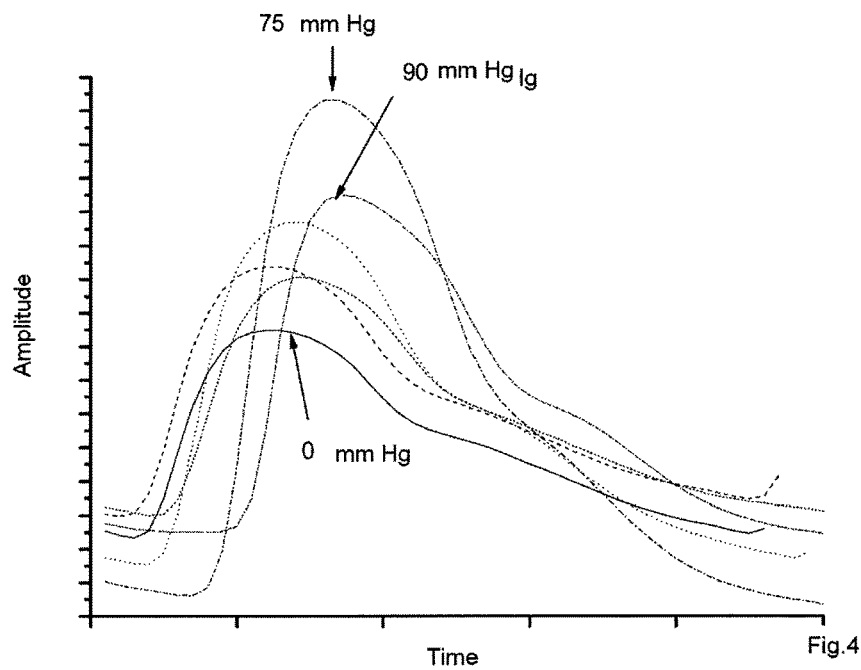
FIG. 4 shows a family of such waveforms recorded at various magnitudes of transmural pressure in patients of the control group.
Figure 5:
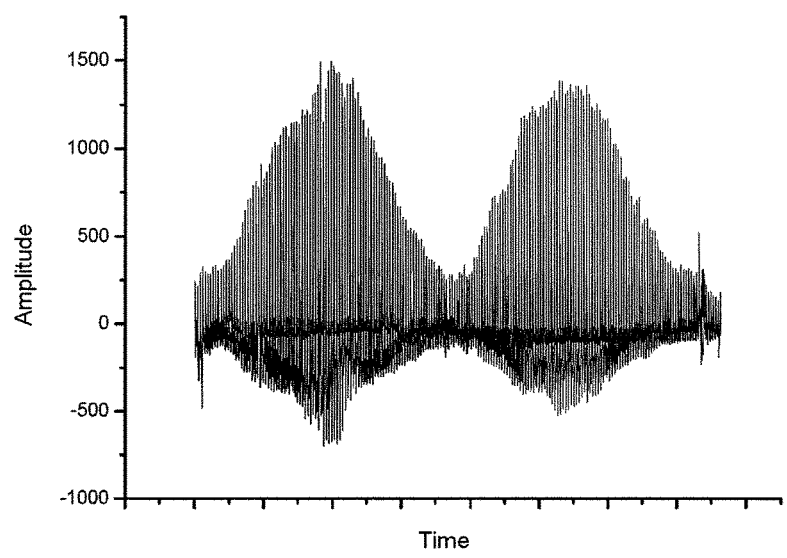
FIG. 5 illustrates the effect of increased hydrostatic pressure on the amplitude of the PPG signal.

Changes in the muscle tone of smooth muscle tissue are expressed not only in the narrowing or dilation of arteries, but also in the increased stiffness or compliance of artery walls. Which the lowering of transmural pressure, the smooth muscle apparatus of blood vessel walls relaxes to a certain extent. This relaxation can be seen on the PPG waveform in the form of an increased signal amplitude. Maximal amplitude is reached when the transmural pressure drops to zero. Schematically this is shown in FIG. 4, where the S-shaped curve reveals that the maximal increase of volume is defined at the point where the transmural pressure is close to zero. When pulse waves are applied evenly to various points on the deformation curve, the maximal plethysmographic signal is observed in the area where transmural pressure is nearing zero. When changing transmural pressure, the amplitude of the waveform can increase by over 100% in patients of the control group. The patients in the control group correspond in age and diastolic blood pressure to the patient group showing symptoms of ischemic disease (FIG. 4). Whereas in the patient group diagnosed with ischemic heart disease, the amplitudal growth does not exceed 10-20%.

This dynamic of the changes in the amplitude of the signal during different transmural pressures can be linked only to particulars of visco-elastic qualities of the arterial channel in healthy individuals as well as in individuals suffering from arteriosclerosis in various locations. The smooth muscle tension of the artery can be considered the predominantly viscous component, while the strands of elastin and collagen clearly serve as the elastic components in the structure of vessel walls. By lowering the smooth muscle tension as the reading of the transmural pressure approaches zero, we lessen the input of the viscous component of smooth muscle to the deformation curve. This detailed technique allows a more thorough analysis of the deformation curve of elastic components of artery vessel walls. Also this technique is more advantageous for recording phenomena of reactive hyperemia which occurs after the occlusion test.

The magnitude of diameter increase in the observed artery is believed to be linked to the functioning of endothelial cells. The increase of the pressure during the occlusion test results in an increase of nitric oxide (NO) production by endothelial cells. This phenomenon is called "flow-induced dilation". If the normal function of endothelial cells is deteriorated, their ability to produce nitric oxide, along with other vaso-active compounds, is diminished. This in turn blocks the vasodilation of vessels. In this situation a full-fledged reactive hyperemia does not occur. At this time this phenomenon is used to reveal the disruption of normal endothelial function, i.e. to reveal endothelial dysfunction.

The flow-induced dilation of the vessel occurs as a result of the following order of events: occlusion, blood flow increase, change in pressure acting on endothelial cells, nitric oxide production (as well as adaptation to the increased blood flow), and finally nitric oxide acting on the smooth muscle.

Figure 1:
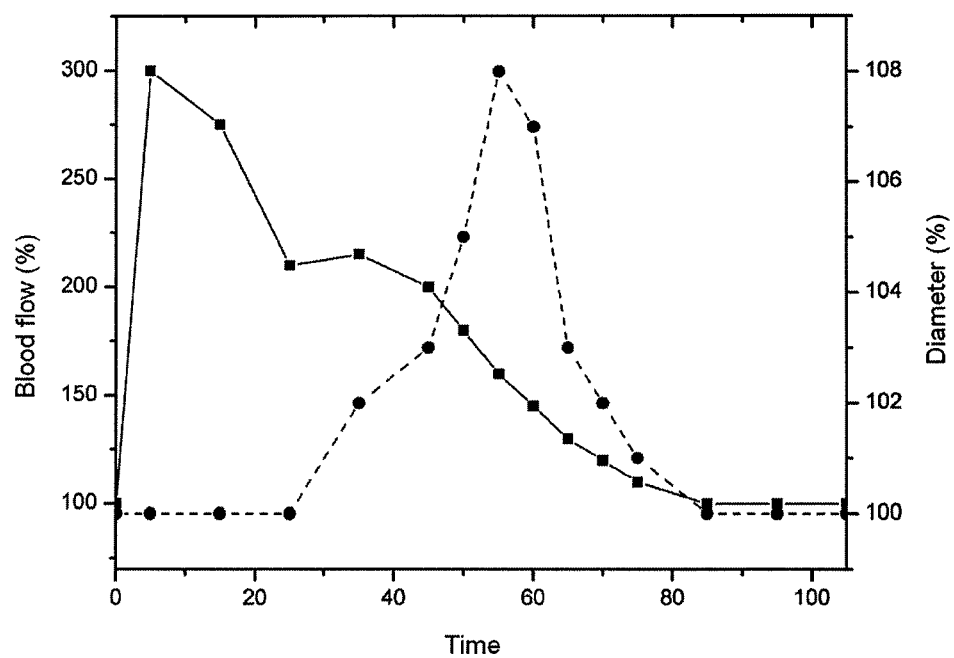
FIG. 1 illustrates the dynamic between measurements of total blood flow and the diameter of the shoulder artery during the occlusion test.

Maximal blood flow volume is reached 1-2 seconds after the removal of the occlusion. It is important to note that during simultaneous monitoring of both blood flow volume and artery dilation, the blood flow increases first and only then does the diameter of the vessel change (FIG. 1). The maximal blood flow speed is reached quickly (within a few seconds), and the increase in artery diameter follows, reaching its maximum in one minute. After that the vessel returns to its original size within 2-3 minutes. Based on the particular state of the elastic module of artery walls in patients suffering from arterial hypertension, it is possible to make an assumption on the potential involvement of excessively stiff arteries in the expression of the endothelial cell response to the occlusion test. One cannot exclude the possibility that with the endothelial cells producing equal amounts of nitric oxide< the response of smooth muscle cells in the artery will be determined by the initial state of the elastic module in arterial walls. In order to normalize the response of the smooth muscle apparatus in arterial walls, it is desirable to have an identical, or if not identical at least similar, level of artery stiffness in various patients. One way to provide a uniform initial state of arterial walls is to select the magnitude of transmural pressure at which the arteries highest level of compliance is reached.

The assessment of the occlusion test results, in terms of reactive hyperemia, can be done not only in the shoulder artery, but in smaller vessels as well.

Figure 2:
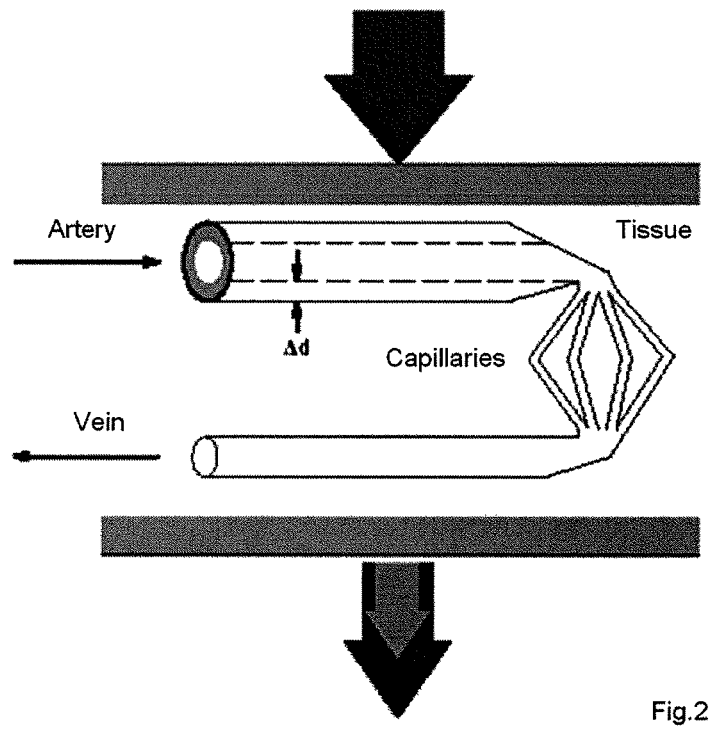
FIG. 2 shows a diagram of the formation of a PPG waveform.

In order to measure flow-dependent dilation, the optical method was used. This method is based on the increase in the observed artery. The incoming pulse wave stretches the artery walls, thereby increasing the diameter of the vessel. Since during the PPG the optical sensor records the increase in blood flow, (rather than changes in the vessel diameter), which is equal to the square of the radius, the measurement can be made with a high level of precision. FIG. 2 shows the method for obtaining the PPG signal. The photo diode records the light stream which passes through the observed region of the finger. As the artery widens with each pulse wave, the volume of blood passing through it increases. Since hemoglobin in the blood absorbs significant amounts of infrared radiation, this reaction leads to an increase in optical density. The pulse wave increases the diameter of the blood vessel as it passes through it. This phenomenon is the main component of the increase of blood volume in the observed region.

Figure 3:
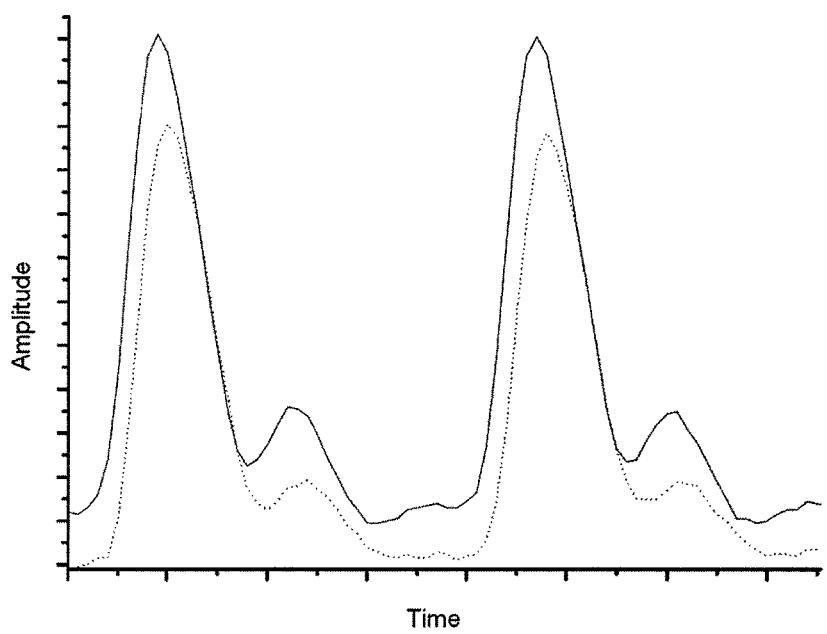

FIG. 3 shows a PPG curve. There are two peaks on the curve—the first represents the contraction of the heart, the second shows the affect of this contraction on the pulse wave. The given curve was obtained with the optical sensor placed on the last of the phalanges of the finger.

Before taking the initial measurements, the compressor (11), following the signal of the control (9), generates a pressure in the cuff (1). The pressure increases gradually, with each step of 5 mmHg lasting 5-10 seconds. As the pressure increases, the transmural pressure drops, reaching zero when the pressure in the cuff equals that of the observed artery. At each step the PPG signal coming from the photoreceptor (3) is recorded. The signal sent from the converter (4) is increased in the amplifier (5) and filtered in the filter (6) where static having the industrial frequency of 50 Hz, along with its harmonics, is screened out. The most significant signal amplification is created by the scalar (instrumental) amplifier. The amplified voltage is sent to the digital analog amplifier (8) and then through the USB interface (10) into the computer. The control (9) determines the pressure at which the signal reaches maximum amplitude. In order to better distinguish between the signal and background static, the measurements are taken synchronously.

The procedure for assessing endothelial activity can be divided into two parts:

1. The transmural pressure is lowered by external pressure applied to a region of the finger (either by the cuff using air, an elastic band, or a mechanical compression), or by changes in the hydrostatic pressure as the extremity is raised to a particular height. The latter procedure can fully replace the pressure applied from the exterior to the vessel wall. In the simplified version of endothelial state assessment, one can eliminate the complex automated system and simply raise and lower the arm. As this is done, one can measure the average blood pressure based on the maximal amplitude of the plethysmographic signal, locate the linear section of the compliancy curve (50% of the maximal growth), and then carry out the occlusion test. The only shortcoming in this approach is the necessity to raise the arm and especially having to run the occlusion test with the arm still in that upraised position.

As the transmural pressure is lowered, the pulse component of the PPG grows. This growth corresponds to the increase in the compliancy of the observed artery. When the gradually-increasing pressure is applied to the finger, one can see the expression of the auto-regulated reaction, and, accordingly, select the optimal conditions (based on the magnitude of the transmural pressure) for the occlusion test (by choosing the steepest part of the curve describing the compliancy of the artery).

2. The artery is closed off by applying super-systolic pressure (of 30 mmHg) for five minutes. After rapidly decreasing the pressure in the cuff set up on the observed artery, the dynamic of the PPG waveform is recorded (with the amplitudal and timely analyses in mind). The changes in the PG signal are recorded simultaneously along the reference and monitoring channels for at least three minutes. During the amplitudal analysis, the magnitude of the amplitudal signal is compared between the reference and monitoring channels, the rate of amplitudal signal increase in the monitoring channel is analyzed, and the relationship between amplitudal signals is established. Also, the maximal amplitude measured during various transmural pressures is compared to the maximal magnitude of the signal recorded after the occlusion test. During the timely analysis the plethysmographic waveforms measured through the reference and monitoring channels, are compared, the signal is normalized, and finally the time of delay or the phase shift is established.

The amplitude of the PPG signal was maximal when the transmural pressure was at zero (that is, the pressure applied to the vessel externally was equal to the average arterial pressure). The calculation was made as follows: diastolic pressure plus $\frac{1}{3}$ of the pulse pressure. This arterial response to the externally applied pressure is not dependent on the state of endothelial tissue. The method of choosing the pressure to be applied externally to the artery allows one to test the dynamic of the PPG waveform at the moment of reactive hyperemia in the most optimal area of the artery's compliancy. Also this method has its own intrinsic diagnostic value: Information concerning the rheological characteristics of the artery can be derived from the measurements of a family of PPG curves that are taken at various transmural pressures. This information helps separate the changes linked to the auto-regulative effect of the smooth muscle apparatus in artery walls when it comes to increasing the artery diameter, from the elastic attributes of the artery itself. The diameter increase in the artery, caused by the increased volume of blood found in the observed region, leads to the growth of the constant component of the curve. The component of the curve which represents the pulse also reflects the increase of blood flow volume into the systole. The amplitude of the PPG is determined by the level of compliancy of the arterial wall as pulse wave pressure passes through it. The open space inside the artery itself does not affect the amplitude of the PPG signal. Despite some observed correlation between the one and the other, a complete correlation between the diameter of the vessel and its level of compliancy during the measuring of the transmural pressure is not observed.

At low transmural pressure the artery wall becomes less stiff than it is at normal physiological levels of arterial blood pressure.

The optimization of the transmural pressure test significantly increases its sensitivity and thus allows the detection of pathologies at the earliest stages of endothelial tissue dysfunction. The high sensitivity of the test will effectively assess the success of pharmacological therapy administered to the patient and directed toward the correction of endothelial function.

When pressure in the cuff was raised to 100 mmHg, the output was also constantly increasing, reaching its amplitudal maximum at 100 mmHg. Further increase in cuff pressure lead to a decrease in the amplitude of the PPG output. If the pressure was lowered to 75 mmHg, the amplitude of the PPG output dropped by 50%. Likewise, pressure in the cuff altered the shape of the PPG waveform (refer to FIG. 3).

The change in the shape of the PPG signal consisted of a delayed yet more rapid and drastic systolic growth. These changes reflect the effect of the cuff on the pressure of the blood passing through the observed vessel. This occurs because the magnitude of pressure cause by the cuff is subtracted from the pulse wave pressure in the vessel.

The raising of the aim above the "point of equal blood pressure" (above the level of the heart) makes the use of externally-applied pressure caused by the cuff unnecessary. When the arm is thus raised above the "point of equal blood pressure" to the point of pointing straight up, the position of the arm increases the amplitude of the PPG output. When the arm is lowered to its initial level the PPG output also decreases to its initial level.

The gravitational force is an important factor affecting the transmural pressure. For instance, the transmural pressure in the digital artery of the raised arm is less than the transmural pressure in that same artery when at the level of the heart. The extent to which the transmural pressure changes depends on the density of the blood, the gravitational force acting on the blood, and the distance that is it from the "point of equal blood pressure".

$$Ptrh = Ptrho - pgh$$

Where Ptrh stands for the transmural pressure in the digital artery of the raised hand, Ptrho—the transmural pressure in the digital artery at the level of the heart, p—the density of blood (1.03 g/cm), g—gravitational force (980 cm/sec.), h—distance from the point of equal blood pressure to the digital artery in the upraised arm (90 cm.). With the given distance from the "point of equal blood pressure" the blood pressure of the person standing with the upraised arm is 66 mmHg lower than the average blood pressure in the digital artery, measured at the level of the heart.

In this manner the transmural pressure can be lowered either by increasing the pressure from exterior or by lowering the pressure in the vessel itself. It is relatively simple to lower the pressure in the digital artery: one has to raise the hand above the level of the heart. By gradually raising the arm we lower the transmural pressure in the digital artery. At the same time the amplitude of the PPG output increases significantly. The average pressure in the upraised arm can drop down to 30 mmHg, whereas when the hand is on the level of the heart, the pressure reads at 90 mmHg. Transmural pressure in the region of the knee can be four times as large as the transmural pressure in the arteries of the raised arm. The effect of the hydrostatic pressure on the magnitude of the transmural pressure can be used when assessing the visco-elastic qualities of the artery wall.

The aforementioned inventions have the following advantages:

1. The pressure for the occlusion test is determined individually for each patient.
2. Information about the visco-elastic attributes of the arterial channel is provided (depending on the amplitude of the PG output derived from blood pressure increase).
3. Provide a clearer relationship between output and noise/static.
4. The occlusion test is done in a more a more optimal region of the compliancy of the vessel.
5. The inventions provide information about the rheological characteristics of the artery by taking and recording sets of PPG waveforms during various transmural pressures.
6. The inventions increase the sensitivity of the test, thereby increasing the reliability of endothelial tissue function assessment.
7. Allow detection of a pathology at the earliest stages of disrupted endothelial function.
8. Allow to reliably assess the effectiveness of prescribed pharmaceutical therapies.

What is claimed is:

1. A method for noninvasive assessment of endothelial function in a patient, which method comprises:
   a. lowering a transmural pressure in an artery in an extremity by means of a pressure generating cuff;
   b. measuring, via a monitoring channel, an amplitude of a plethysmographic signal at various transmural pressures generated in step (a);
   c. determining a pressure in the pressure generating cuff at which the amplitude of the plethysmographic signal is maximal;
   d. lowering the pressure in the pressure generating cuff to 50% of the pressure at which said maximal amplitude occurs;
   e. when the pressure in the pressure generating cuff is 50% of the pressure at which said maximal amplitude occurs, running an occlusion test; wherein running an occlusion test comprises generating a pressure in the pressure generating cuff on an observed region of the extremity which exceeds a measured systolic pressure by at least 50 mmHg for at least 5 minutes;
   f. lowering the pressure in the pressure generating cuff to zero;
   g. measuring an amplitude of the plethysmographic signal for at least 3 minutes and simultaneously measuring, via a reference channel, an amplitude of a plethysmographic signal detected from an artery in a second extremity where the occlusion test has not been performed;

h. using amplitudal and timely analyses to compare data collected through the reference and monitoring channels; and i. providing an assessment of the patient's endothelial function based on the amplitudal and timely analyses.

2. The method according to claim 1, wherein pressure applied to the extremity is increased gradually, with each step being 5 mmHg and lasting 5-10 seconds, at the same time recording the amplitude of the plethysmographic output.

3. The method according to claim 1, wherein (i) during the amplitudal analysis data from the reference channel are compared to those collected from the monitoring channel; (ii) a rate of the increase of the amplitude in the monitoring channel is analyzed; (iii) a relationship of an amplitude of a maximum plethysmographic signal recorded during various transmural pressures is compared to a maximal amplitude of a plethysmographic signal recorded after the running of the occlusion test; and/or (iv) during the temporal analysis, plethysmographic waveforms collected through the reference and monitoring channels are compared, the plethysmographic waveforms are then normalized and a time delay or phase change is determined.

4. An apparatus for noninvasive assessment of endothelial function comprising a double-channeled sensor unit, capable of detecting pulse wave signals from peripheral arteries, a pneumatic unit capable of creating gradually increasing pressure in a pressure generating cuff, a pressure sensor configured to detect a blood pressure of a patient; and an electronic block configured to perform at least the following steps:

a. lowering a transmural pressure in an artery in an extremity by means of a pressure generating cuff;

b. measuring, via a monitoring channel, an amplitude of a plethysmographic signal at various transmural pressures generated in step (a);

c. determining a pressure in the pressure generating cuff at which the amplitude of the plethysmographic signal is maximal;

d. lowering the pressure in the pressure generating cuff to 50% of the pressure at which said maximal amplitude occurs;

e. when the pressure in the pressure generating cuff is 50% of the pressure at which said maximal amplitude occurs, running an occlusion test wherein running an occlusion test comprises generating a pressure in the pressure generating cuff on an observed region of the extremity which exceeds a measured systolic pressure by at least 50 mmHg for at least 5 minutes;

f. lowering the pressure in the pressure generating cuff to zero;

g. measuring an amplitude of the plethysmographic signal for at least 3 minutes and simultaneously measuring, via a reference channel, an amplitude of a plethysmographic signal detected from an artery in a second extremity where the occlusion test has not been performed; and h. using amplitudal and timely analyses to compare data collected through the reference and monitoring channels;

wherein the double-channeled sensor unit is connected to the electronic block, which is in turn linked through an outlet to the pneumatic unit.

5. The apparatus according to claim 4, wherein the pneumatic unit is capable of generating pressure in the pressure generating cuff which is increased gradually by increments of 5 mmHg with time increments of five to ten seconds.

6. The apparatus according to claim 4, wherein each channel of the double-channeled sensor unit comprises an infrared diode and a photoreceptor, both configured to record a light signal passing through an observed field.

7. The apparatus according to claim 4, wherein each of the channels of the double-channeled sensor unit comprises an infrared light diode and a photoreceptor, both configured to record a diffused light signal reflected off an observed field.

8. The apparatus according to claim 4, wherein (i) the double-channeled sensor unit comprises impedancemetric electrodes, or Hall sensors, or an elastic tube filled with electro-conductive material; or (ii) it additionally comprises orthogonally-placed polarized filters protecting the photoreceptor from extraneous exposure to light.

9. The apparatus according to claim 6, wherein the photoreceptor is connected to a filter configured to filter pulse wave components out of a general signal.

10. The apparatus according to claim 4, further comprising a liquid-crystal screen for displaying results of endothelial tissue assessment, and/or an interface system connected to the electronic block for transferring collected data to a computer.

11. The apparatus according to claim 4, wherein lowering the pressure in the pressure generating cuff to 50% of the pressure at which said maximal amplitude occurs comprises providing optimal arterial compliance.

* * * * *